(12) United States Patent
Gómez et al.

(10) Patent No.: US 6,723,323 B1
(45) Date of Patent: Apr. 20, 2004

(54) VIBRIO CHOLERAE VACCINE CANDIDATES AND METHOD OF THEIR CONSTRUCTING

(75) Inventors: Javier Campos Gómez, Villa Clara (CU); Rafael Alfredo Fando Calzada, Ciudad Habana (CU); Boris Luis Rodríguez Gónzalez, Ciudad Habana (CU); Edgar Valle Díaz, Camaguey (CU); Talena Yamilé Ledón Pérez, Ciudad Habana (CU); Anisia Juana Silva, Fresno, CA (US); Jorge Antonio Benitez Robles, Fresno, CA (US)

(73) Assignee: Centro Nacional de Investigaciones Cientificas, (CNIC) (CU)

( * ) Notice: Subject to any disclaimer, the term of this patent is extended or adjusted under 35 U.S.C. 154(b) by 0 days.

(21) Appl. No.: 09/582,772

(22) PCT Filed: Dec. 30, 1998

(86) PCT No.: PCT/CU98/00008

§ 371 (c)(1),
(2), (4) Date: Dec. 4, 2000

(87) PCT Pub. No.: WO99/35271

PCT Pub. Date: Jul. 15, 1999

(30) Foreign Application Priority Data

Dec. 30, 1997 (CU) .............................................. 142/97

(51) Int. Cl.$^7$ .......................... A61K 39/02; A61K 48/00; A61K 39/106; A01N 63/00; C12N 15/64

(52) U.S. Cl. .................. 424/200.1; 424/93.4; 424/93.2; 424/261.1; 424/184.1; 435/69.3; 435/91.42; 435/471

(58) Field of Search ............................. 424/200.1, 93.4, 424/184.1, 236.1, 261.1, 93.61, 203.1; 435/69.3, 91.6–91.42, 471

(56) References Cited

FOREIGN PATENT DOCUMENTS

| EP | 0251579 A2 | * | 1/1988 |
| WO | WO 99/61634 A1 | * | 12/1999 |

OTHER PUBLICATIONS

Attridge SR. Microbial Pathogenesis 19: 11–18, 1995.*
Robert et al. Vaccine 14: 1517–1522, 1996.*
Rijpkema et al. Infect. Immun. 60: 2188–2193, 1992.*

* cited by examiner

*Primary Examiner*—S. Devi
(74) *Attorney, Agent, or Firm*—Lackenbach Siegel LLP

(57) ABSTRACT

*Vibrio cholerae* vaccine strains which have a disrupted hap gene and which are tagged with celA coding functions from *Clostridium thermocellum* are described. A contained, genetically defined thyA mutant of *Vibrio cholerae* and the general methodology of making along with the sequence of thyA gene are also described.

3 Claims, 4 Drawing Sheets

VIBRIO CHOLERAE VACCINE CANDIDATES AND METHOD OF THEIR CONSTRUCTING

TECHNICAL SECTOR

Figure 1:
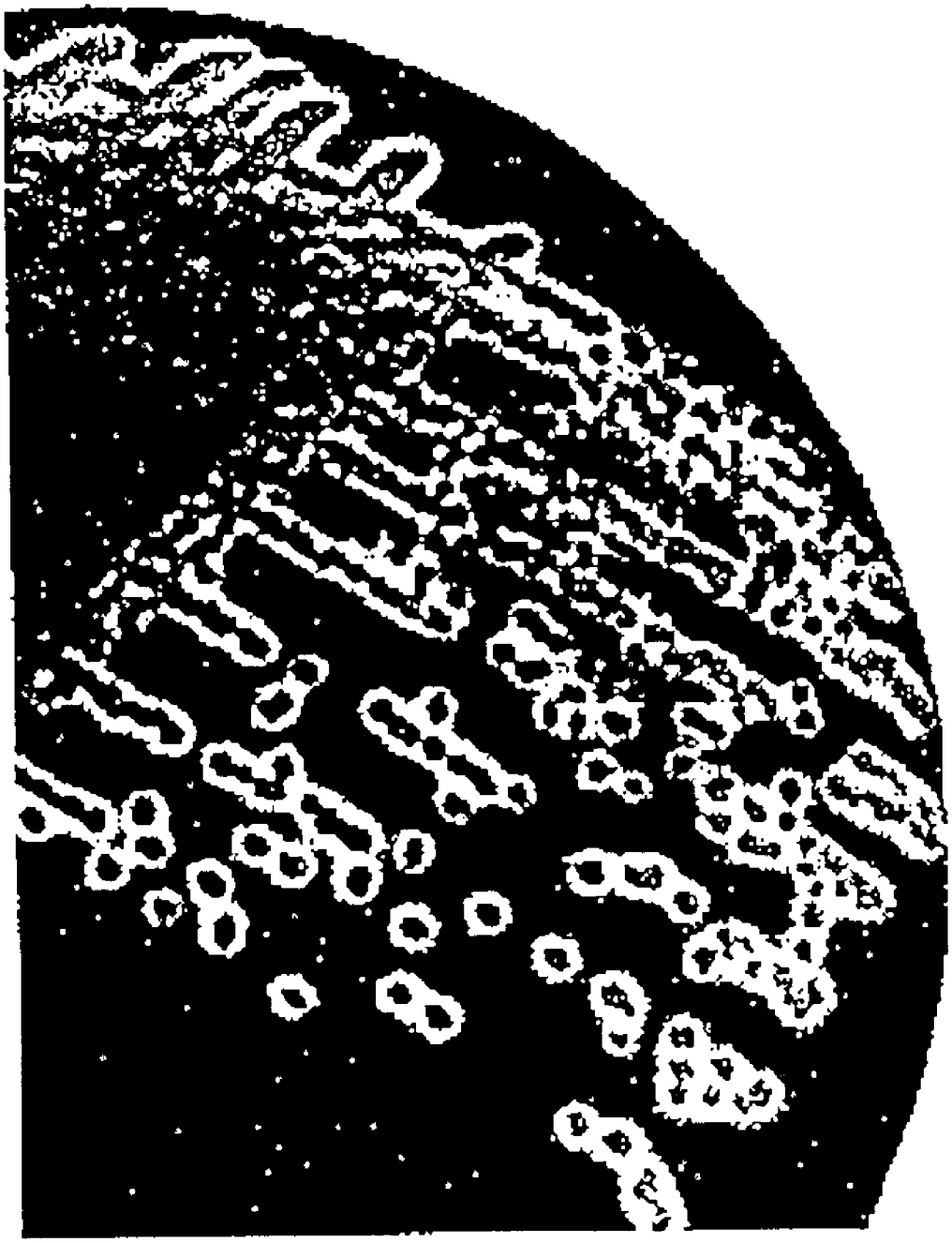

The field of invention is that of Biotechnology and more specifically the generation of *Vibrio cholerae* vaccines and the methods of constructing them by using genetic engineering tools.

BACKGROUND OF THE INVENTION

A brief explanation on the terminology used through the text of the invention is listed below.

By ctxΦ virus is meant the particle of protein-coated DNA, produced by certain *Vibrio cholerae* strains, which is capable of transducing its DNA, comprising cholera toxin genes, to other *Vibrio cholerae* strains.

By cholera toxin is meant the protein responsible for the clinical symptoms of cholerae when produced by the bacteria.

By ctxΦ-encoded toxin genes are meant, in addition to cholera toxin genes, zot and ace genes, which code for the "zonula occludens toxin" and for the "accessory cholera enterotoxin", respectively.

For non-toxigenic strains of *Vibrio cholerae* it most be understood any strain devoid of the genes coding for the above toxins, which are as well, useful as vaccines but still produce an undesired reactogenic syndrome.

The term safe vaccine or safe strain refers to such strain lacking the residual reactogenicity of non-toxigenic strains of *Vibrio cholerae*.

By hemagglutinin/protease is meant the protein manifesting dual function, being one of them the ability to agglutinate erythrocytes from certain species and the other the property to degrade proteins such as mucin.

The term celA refers to the nucleotide sequence coding for the endoglucanase A protein. This protein naturally occurs in *Clostridium thermocellum* strains and has a β(1-4) glucan-glucane hydrolytic activity able to degrade cellulose and its derivatives.

By Thymidylate synthase is meant the protein capable of catalyzing the reductive methylation of deoxyuracil monophosphate (dUMP) by $N^5$-$N^{10}$-methylene-tetrahydrofolate to yield 2,5 deoxythymidyne phosphate (dTMP) and dihydrofolate.

Substantially pure DNA is DNA that is free from both of the coding sequences immediately contiguous by the 5' or the 3' end of thyA coding sequence, in the naturally occurring genome of the microorganism from which the DNA of the invention is derived. The term thereof includes, for example, a recombinant DNA which is incorporated on a vector strain, cell line or plasmid, or which exists as a separate molecule (e.g., cDNA, restriction or PCR fragment). It also includes recombinant DNA molecules which are part of a hybrid gene encoding additional sequences.

Homologous sequences refers to DNA or protein sequences which share similar or identical residues being nucleotides or amino acids, respectively, in identical positions of two or more given strings. The greater the number of identical/similar residues in certain position, the greater the percent of identity/similarity between two them.

Clinical cholera is an acute diarrheal disease that results from an oral infection with the bacterium *Vibrio cholerae*. After more than 100 years of research on cholera there remains the need for an effective and safe vaccine. Humankind has witnessed seven pandemics of cholera; the former six were caused by strains of the classical biotype and the current seventh pandemic is characterized by the predominance of Vibrios belonging to El Tor Biotype. Recently, beginning in January of 1991, this pandemic has extended to South America causing greater than 25 000 cases and over 2000 deaths in Peru, Ecuador, Colombia, and Chile. By November 1992, a new serogroup emerged in India and Bangladesh, the O139, showing a great epidemic potential that became a new cause of concern throughout the developing world. These recent experiences reinforce the need for effective cholera vaccines against disease caused by *V. cholerae* of serogroups O1 (El Tor) and O139.

Because convalescence to cholera is followed by an state of immunity lasting at least 3 years, much of the efforts in *Vibrio cholerae* vaccinology have been made to produce live, attenuated cholera vaccines, that closely mimic the disease in its immunization-prbperties after oral administration, but do not result reactogenic to the individuals ingesting them. Vaccines of this type involve deletion mutations of all toxin genes encoded by the ctxΦ Vibriophage. See patents of Kaper, J. et al.; WO 91,18979 and Mekalanos, J., WO 95,18633).

The first vaccine to be assayed against cholera dates from 1885–1892. It was a traditional vaccine that comprised administration by parenteral route of "attenuated" vibrios. It resulted limited in efficacy and unacceptably reactogenic (Finkelstein R. A., International Symposium on Cholera on the America Continent. Sao Paulo, SP, Brasil, 1992). Oral vaccination was tried first in 1892, using attenuated *Vibrio cholerae* strains. The results of this attempt were misinterpreted and the strategy immediately abandoned. Oral vaccination was later rescued in 1970–1980 at the Center for Vaccine Development of Maryland, USA, by using chemically mutagenized vibrios as immunizing agents. Reversion to virulence of these mutants impeded further spread of the strategy (Levine et al., Infect and Imm, No 2, 1984; Finkelstein et al., patent U.S. Pat. No. 4,328,209) and prompted the researchers to generate genetically defined non-toxigenic mutants unable to revert. Although these mutants have shown to confer solid immunological protection against disease (Kaper J. B. and Levine M. Patents U.S. Pat. No. 06,472,276 and U.S. Pat. No. 581,406), the essential drawback for their use is the high level of adverse reactions they produce in vaccinees (Levine et al., Infect. and Imm. Vol 56, No 1, 1988). According to these data the major issue to be overcome when producing an effective cholera vaccine is safety. Additionally, researches worldwide are currently concerned on the horizontal transfer of genetic information among bacteria, thus it is necessary to pay attention to this aspect when designing live bacterial vaccines, with the aim to ameliorate the environmental impact during vaccination. It is also necessary to achieve good levels of stability and immunogenicity.

A dead cholerae vaccine consisting of whole cells supplemented with the B subunit of cholera toxin is available (Holmgren et al., Current topics in Microbiology and Immunology, Vol. 146, 1989). Such vaccine is safe and effective but requires multiple doses to generate an immune response equivalent to that of a cholera infection and consequently is very expensive.

Another alternative for cholera vaccination is the recent licensed CVD103-HgR, a live cholera vaccine belonging to the classical biotype. It is safe, effective and cheap; however its protective efficacy against the current circulating El Tor and O139 vibrios is not as good as against Classical vibrios (See patent U.S. Pat. No. 5,399,494).

Other live vaccine candidates have been described in patent WO 95/18633. Such mutants represent all serotypes of the current pandemic, including the O139. They are safe, their production is cheap, and have been shown to be preliminary effective; however they are not as extensively tested as CVD103-HgR. All these candidates are protothrophic bacteria able to survive natural conditions of the environment. Additionally, although a procedure to obtain defined mutants is described in the document, the proposed candidates constitute non-motile spontaneous mutants. It has been proposed by the inventors that the non-motile nature of these vaccine candidates limits their ability to reach the enterocyte surface and avoid the elicitation of the reactogenic response characteristic of their parentals.

Finkelstein et. Al, J. Bacteriology, Vol. 173, No. 11, 3311–17, cloned and sequenced the gene coding for the Hemagglutinin/Protease (hap). The mutan: HAP-1 was additionally isolated by insertional inactivation of this gene with a kanamycin resistance cassette in the bacterial chromosome. Rather than for vaccine purposes, thisstrain was a fundamental research approach. Finkelstein et. Al, Infection and Immunity, Vol. 60, No. 2, 472–78 demonstrated that wild type and hap mutants were virulent to the same extent, concluding that the hap gene product was not directly involved in virulence. In this paper, the authors provide results to support the conclusion that HA/P is a "detachase" which could act to destroy host cell receptors for different adhesins of *V.Cholerae*. Despite this knowledge, no mutants in this gene were construted for vaccination purposes.Robert et al., Vaccine, Vol. 14, No 16, 1517–22, 1996, demonstrated the factibility of using the hemagglutinin/protease locus for the insertion of heterologous tags, without detriment of the colonizing capacity of vibrios. Colonization of the human small bowel by *Vibrio cholerae* is essential to induce a strong localized immune response of secreted IgA in the intestinal mucosa and to produce a long lasting immunity against cholera (Taylor et al., The Journal of Infectious Diseases, 1994, 170: 1518–23).

It has been wisely sustained by Dr. Mekalanos, that uptake of bacteria by Peyer's patches is a consequence of the colonization process that does not lead to reactogenicity and is considered an essential step in the localized immune response pathway. In contrast, the interaction of bacteria with enterocytes results in adverse reactions unacceptable for vaccine purposes (Mekalanos J. et al., Bull. Inst, Pasteur, 93: 255–262, 1995). According to this criteria mutations that interfere with the capacity of vibrios to reach the enterocytes are desired features of cholera vaccines.

DESCRIPTION OF THE INVENTION

*Vibrio cholerae* mutants, despite having deletions in the cholera toxin genes (atoxigenic mutants), still produce unacceptable levels of reactogenicity in humans, which has precluded the use of several live attenuated mutants for vaccination. This invention issues a method to abolish the residual reactogenicity of non-toxigenic mutants of *Vibrio Cholerae* by inactivation of the hemagglutinin/protease gen (hap), which is useful to obtain a safer, genetically defined, and stable mutant of *Vibrio cholerae* useful as a live, oral vaccine for inducing immunological protection against cholera in humans. Such mutant derives from a non-toxigenic strain of *Vibrio cholerae* by disruption of the hemagglutinin/protease gene (hap) with the marker gene celA. In preferred embodiments of this document the vaccine strain belongs to either of the two serotypes of the El Tor Biotype or to the O139 serotype of *Vibrio cholerae*. Preferably this strain derives from a non-toxigenic mutant of *Vibrio cholerae*, obtained by means of genetic engineering tools and is tagged with the marker gene celA within the hap locus. In the most preferred fashion the strain is 638, 1333, or L911.

This invention additionally includes a method to enhance the environmental biosafety of any strain of *Vibrio cholerae* intended to be used as a live or as the source for large scale production of dead vaccines. The method described herein involves cloning and genetically manipulating the thyA gene to perform an internal deletion, and the exchange of the wild type copy in the chromosome by the mutated allele created "in vitro".

Among preferred embodiments of this invention results any vaccine strain of *Vibrio cholerae* belonging to existent biotypes and serotypes or any emergent serotype against which current vaccines are not effective and which has been obtained by means of genetic manipulations in the genes coding for HA/P and Thymidilate Synthase, to render a double mutant with improved environmental biosafety features. More preferably the mutant is a derivative of 81, 413 or SG251a, and in the most preferable way the strain is 638T or the thyA$^-$ derivatives of 1333 and L911. As well this contained version of vaccine strains is useful as an entity for antigen delivery to the mucosal immune system.

We have found such mutants to be low reactogenic in laboratory and/or clinical tests, although yet able to elicit strong immune responses when administered by oral route. As a result these hemagglutinin/protease defective mutants and their further derivatives share the desirable properties for a vaccine against cholera in humans.

Additionally, the invention provides substantially pure DNA encoding the thyA gene for *Vibrio cholerae* Thymidilate Synthase. By thyA DNA is meant the DNA sequence shown as SEQ ID NO 1, and fragments, deletions, disruptions and homologous sequences thereof.

The construction of vaccine strains described herein involves replacement of the chromosomal gene coding for the wild type Hemagglutinin/Protease by a celA disrupted allele in non-toxigenic mutants of *Vibrio cholerae* having deleted all genes encompassing the ctxΦ prophage. These mutants are genetically well defined and very stable in their proteolytic defect, showing no reversion detectable in $10^9$ cells. Said mutants are equally stable in their cellulolytic activity conferred by the celA chromosomal marker, even after passage by the intestine of mice or humans.

Construction of further derivatives with enhanced environmental biosafety features involves introducing a genetic deletion in the thyA gene of the mutant, to obtain a thymine/thymidine auxotrophic derivative. The resultant triple mutant is genetically well defined and stable. As a consequence of this mutation the strain is provided with a resistance marker to the antibiotic trymethoprim, which is conditioned to the presence of thymine/thymidine. Such marker is unlikely to transform other bacteria by horizontal transfer due to its recessive nature.

This invention issues non-toxigenic, genetically defined, stable, and safe mutants of *Vibrio cholerae* which are useful as a live, oral vaccines for inducing immunological protection against cholera in humans. When designing our non-reactogenic cholerae vaccine candidates we have stuck to the idea of reactogenicity as a consequence of interaction between *Vibrio cholerae* and enterocytes. We reasoned that inactivation of the major secreted protease, responsible for mucin degradation, would render a strain of *Vibrio cholerae* inefficient in penetration of the thick mucous layer of the enterocytes, but unchanged in the ability to reach the surface of the M cell and elicit a strong immune response. The major secreted, mucin degrading protease in strain C7258, C6706 and SG25-1 was found to be the soluble hemagglutinin/protease, a putative virulence factor described by Finkelstein, et al. Journal of Bacteriology, Vol. 173, No. 11, pp. 3311–3317, 1991. Paralleling the inactivation of the hemagglutinin/protease gene, a DNA fragment coding for the endoglucanase A of Clostridium thermocellum was inserted in the Vibrio cholerae chromosome. This mutation combined with the deletion of cholerae toxin genes of the ctxφ genome resulted in tagged vaccine candidates with excellent properties as immunizing agents for vaccinating humans against cholera. The essential finding for this application was that disruption of hap in our non-toxigenic strains removed their residual reactogenicity.

As an example, rather than as an interest to be limiting; the non-toxigenic mutants of Vibrio cholerae useful for constructing safe mutants defective in the expression of hemagglutinin/protease for vaccine purposes, are described in table 1a. Non-toxigenic mutants are specifically characterized by the absence of all ctxφ coding sequences in their chromosome, and by the presence of a single RS1 element, the nucleotide sequence of which was confirm by DNA sequencing. The methods of producing non-toxigenic mutants of Vibrio cholerae are well described elsewhere (Archives of Medical Research, 27, No. 3, pp. 275–283, 1996).

TABLE 1a

Starting strains for constructing HA/P defective mutants.

| Vaccine candidate | Biotype/Serotype | Genotype |
|---|---|---|
| 81 | El Tor/Ogawa | Δctxφ |
| 413 | El Tor/Inaba | Δctxφ |
| SG25-1[a] | O139 | Δctxφ |

All strains and the methods of making are described in Archives of Medical Research, Vol. 27, No. 3, pp. 275–283, 1996. 81 and 413 derive from C7258 and C6706, respectively; both of which are clinical isolates from Perú, 1991. SG25-1 a is a derivative of the O139 isolate SG25-1 from Calcutta, India, 1993.

In a similar way, table 1b provides the hemagglutinin/protease mutants useful for constructing thyA defective derivatives with better features of biosafety.

TABLE 1b

Hemagglutinin/Protease mutants useful for constructing thyA mutants.

| Vaccine candidate | Relevant properties |
|---|---|
| 638 | 81 hap::celA |
| 1333 | 413 hap::celA |
| L911 | SG251 a hap::celA |

Characterization of Non-toxicenic Vaccines With Additional Mutations Intended to Enhance Their Biosafety Serological Characterization.

After any new mutation was introduced in vaccine strains described herein the derivative was demonstrated to retain the expected serotype. Cells were harvested from a plate, suspended in saline and immediately tested with Difco typing serum specific for Inaba, Ogawa or O139.

The major immune response elicited by vaccinees is directed against the LPS of the bacterium. All strains being issued in the present invention retained expression of the expected O-antigen as confirmed by serological tests. Additionally LPS profiles remained unchanged in polyacrylamide gel electrophoresis and Western blot.

Infant Mouse Colonization Assay.

The infant mouse colonization assay (Herrington et al, J. Exper. Med. 168:1487:1492, 1988) was used to asses the colonization properties of each mutant. An inoculum of $10^5$–$10^6$ vibrios in a final volume of 50 μl was administered intragastrically to groups of at least five mice. After 18–24 hours at 30° C., mice were sacrificed, the intestine was dissected, homogenized and plated on bacteriological media containing appropriate supplements to support growth of mutants. Colonies that grew after overnight incubation were tested for additional markers.

The ability of doubly and triply mutated (Δctxφ, HA/P)/(thyA⁻) strains of Vibrio cholerae to colonize the intestine of suckling mice can be observed in table 2. Strains 638, 1333 and 638T are well colonizers of the small bowell of mice. Colonization of gastrointestinal tract of infant mice is widely accepted to correlate well with colonization of the human gut, which is necessary to prime the mucosal immune system and to induce a strong secretory IgA response. Although L911 colonizes less eficiently than the rest it is still able to colonize.

It should be noted that 638T is a thyA⁻ mutant of 638. The mutation introduced in this strain creates a thymine or thymidine dependence that reduces the ability of this strain to multiply in natural environments where free pyrimidines are usually absent from.

TABLE 2

Colonizing capacities of hap::celA vaccine strains.

| Strain | Input | Output | Biotype/Serotype | Relevant genotype |
|---|---|---|---|---|
| 638 | $1 \times 10^6$ | $2.8 \times 10^5$ | El Tor/Ogawa | Δctxφ, hap::celA |
| 1333 | $2 \times 10^6$ | $4.2 \times 10^5$ | El Tor/Inaba | Δctxφ, hap::celA |
| L911 | $1.2 \times 10^6$ | $8 \times 10^3$ | O139 | Δctxφ, hap::celA |
| 638T | $1.7 \times 10^6$ | $6 \times 10^5$ | El Tor/Ogawa | Δctxφ, hap::celA, thyA⁻ |

Detection of Protease Activity.

Milk-LB plates were used to detect proteolytic activities in supernatants of TSB-grown vibrios. For quantitation of protease activity the azocasein method was adapted from Ginther C L., Antimicrob. Agents Chemother. 15, 522–526, 1979. Briefly 1.1 ml of buffer ($CaCl_2$ 1 mM; Tris 0.2M, pH 7.2; Azocasein 1%); were mixed with 200 μl of culture supernatant and incubated for 1 hr at 37° C. The unreacted substrate was precipitated with 83 μl of TCA 40% for 10 min. followed by 10 min. centrifugation at 12000 rpm. The colored product remaining in solution was neutralized with NaOH and read at 450 nm. One unit of enzymatic activity was defined as the quantity of enzyme producing a net increase of one in the optical density of the sample in one hour of reaction.

The mutation introduced in the hemagglutinin/protease gene of strains disclosed herein, accounts for a reduction in 60–80% of the proteolytic activity as observed in mutants when compared to their non-toxigenic parents.

Detection of Vibrios Expressing the Endoglucanase A Marker

For CelA activity detection, vibrios were grown in LB plates for 24 hours, overlayed with CMC-indicator agar and incubated for 4 hours at 60° C. Endoglucanase A positive colonies were visualized after Congo Red staining and washing, as red colonies surrounded by a transparent halo in the red background of the plate. CMC-indicator agar was composed of 0.7% agarose, 0.5% CM-cellulose in phosphate-citrate buffer pH 6.3 and staining solution was 1% Congo Red in water.

The celA marker used to unequivocally distinguish the vaccine, is stably expressed and inherited in *Vibrio cholerae*. The appearance of tagged vibrios can be observed in FIG. 1.
Scoring for a Thymidine Auxotrohpy in Vaccine Strains Generated by Specific Mutagenesis of thyA Gene M9-salts supplemented with glucose as the carbon source and thymine/thymidine (200 $\mu$g/ml) were used to detect growth of thyA defective mutants impaired to grow in M9-salts glucose medium. LB plates supplemented with 200 $\mu$g/ml of thymidine were used to check for trimethropim resistance in the thyA mutants generated. The stability of thymidine auxotrophy was analyzed by replica-plating colonies from M9-glucose-thymidine to M9-Glucose plates.

Strains 638,1333, and L911 are prototrophic bacteria able to grow in mineral salts employing glucose as the sole carbon source. Strain 638T requires addition of thymidine or thymine for growth in minimal medium. When one of these supplements is present 638T is resistant to up to 200 $\mu$g/ml of trimethoprim.

Assay for Motility.

Cells from single well isolated colonies were picked from a master plate aided with the tip of a platinum needle and inoculated by insertion (2–3 mm) into a motility agar plate (LB, agar 0.4%). The diameter each colony spreaded through soft agar was recorded at 24 hours of incubation at 30° C. The criteria for motility was as follows. A bacterial strain spreading 3 mm or less from the point of application was considered non-motile. A bacterial strain spreading >3 mm beyond the point of inoculation was considered motile.

All strains under the scope of this patent, but L911 were found to be motile. L911 is a derivative of SG251, which in our hands, resulted non-motile when assayed in motility agar.

Assay for Flagella

Motile and non-motile bacteria were assayed for the presence of flagella by electron microscopy. Briefly, *Vibrio cholerae* was grown for 4 hours at 37° C. on colonization factor antigen agar (CFA, casaminoacids, 1%; Yeast extract, 0.15%; Magnesium Sulphate, 0.05%; Manganesium Chloride, 0.005%), harvested and washed in saline (NaCl, 0.9%). Bacteria were negatively stained with 1% uranyl acetate for 3 min. and analyzed by transmission electron microscopy.

The flagellate nature of bacteria was also demonstrated for all vaccine strains as above, with greater emphasis on non-motile O139 strain L911 (FIG. 2). All strain described herein were shown to be flagellated, including the non-motile L911.

Assays for TCP

Mutant strains were examined for the presence of toxin corregulated pilus on bacterial surface by immunogold electron microscopy. Cells were cultured as for the assay of flagella. Fresh harvested suspensions of vibrios were (10 $\mu$l) deposited on a carbon coated nickel grid, fixed for 1 min. by exposing the grid to a 60 watts lamp and the excess of liquid removed on a filter pad. The grid was inverted in a drop of a TCP-specific sera diluted in saline, 1% BSA, 0.05% Tween® 80, incubated during 15 min. for reaction and washed in saline-BSA-Tween®. Washed grids were incubated with the gold labeled conjugate diluted in the same buffer, let to stand for 15 min. and washed 3 times with saline-BSA-Tween®. After washing, samples were stained during 1 min with a 1% ammonium molibdate solution.

The most important features of cholera vaccines are safety and antigenicity. By genetic manipulation, *V. cholerae* strains are rendered safe, but care should be taken to retain their antigenicity unchanged. *Vibrio cholerae* strains disclosed in the preset patent application were evaluated for the expression of most prominent antigens in the bacterium. TCP was visualized on bacterial surface by immunogold electron microscopy. Alternatively, expression of this key colonization factor was detected by Western analysis. All strains analyzed (e.g. 638, 1333, L911 and 638T) produced normal levels of TCP protein and assembled it into large appendages on bacterial surface (FIG. 3).

Live Vaccine Strains

Strains 638, 1333, L911 and 638T described herein, can be used to achieve adequate immunological protection against cholerae in humans, provided the high rates of seroconversion they elicit and the low levels of adverse reactions they produce when orally administered to human volunteers. Depending upon relevant local epidemiology a single strain or combinations of them could be used for immunization.

Culturability of Vaccine Strain

Vaccine strains were cultured in standard laboratory medium. Suplements of thymidine (200 $\mu$g/ml) were added when necessary for growth, but no supplements were included in the inoculum.

Dosage

A single oral dose of live vaccine was administered to people in bicarbonate buffer (2%) after harvesting bacteria from a fresh plate in aseptic saline (NaCl 0.9%). Useful inoculum are $10^7$–$10^9$ cells per immunizing dose. Alternatively more than one dose, separated 7–28 days apart, can be given to each subject. Preferably vibrios can be lyophilized in a formulation that preserves viability and mixed with bicarbonate prior to inoculation.

Clinical Testing of 638.

Strain 638 has been tested in human trials involving 42 volunteers aged 18–40. A summary of clinical findings after ingestion of strain 638 and placebo is shown in Table 3. All clinical manifestations observed were mild and of short duration. No statistical significance could be demonstrated between the inoculated and placebo groups with the present data. Gurgling and abdominal cramps were the reactions more frequently reported by volunteers irrespective of dose. Four volunteers developed mild diarrhea (grade 3). Three of these volunteers received the high dose and one the medium dose. One volunteer who received the high dose, had 5 loose stools (72 h after inoculation) and a total output of 680 g. Two volunteers had 2 loose stools 28 and 72 h after inoculation with total outputs of 220 and 500 g, respectively. The other volunteer had a single diarrheal output of 300 g 73 h after inoculation.

Bacteriological Isolation of Vaccine Strain.

As indicated in Table 4, strain 638 was recovered in 37 out of 42 volunteers inoculated (88%). For the higher dose, excretion of the vaccine strain tend to peak at 72 h after inoculation. Three out of the 4 cases of diarrhea occurred at this time. Of the 37 volunteers that excreted vibrios, 12 excreted on at least 4 days, 19 on at least 3 days, and 28 on 2 days. The number of volunteers excreting strain 638 and the mean number of vibrios/g stool declined in the lower dose. Vibrios isolated from the stool of volunteers produced endoglucanase A indicating that the celA reporter gene was stably maintained during growth in the human intestine. We conclude that strain 638 is a good colonizer of the human small bowel.

Immune Response to Vaccine Strain.

Strain 638 elicited a significant and consistent immune response in terms of serum vibriocidal antibodies, serum anti-Ogawa LPS IgG or IgA, and Ogawa LPS-specific IgA ASC (Tables 5 y 6). Although reciprocal GMT peaked 14 days after inoculation, seroconversion was attained on day 7 and titers remained high till day 28. Seroconversion rates, peak reciprocal GMST, and ELISA titers were dose-dependent. However, even at the lowest dose, strain 638 elicited a significant vibriocidal antibody response compared to placebo. A significant proportion of the volunteers which experimented seroconversion developed relatively high ($\geq 1024$) vibriocidal titers (Table 6). The high percentage of responders in the ASC evaluation (Table 5) reflects an effective stimulation of mucosal immunity, mainly sIgA, by strain 638 in correspondence with the elevated anti-LPS IgA titers encountered 14 days after inoculation. One volunteer who ingested placebo seroconverted for anti-LPS lgG. This volunteer had very low pre-inoculation anti-LPS serum IgG which increased to the cutoff value at day 7 and remained constant thereafter. Another volunteer who ingested placebo reached the cutoff value of ASC. Similarly, this volunteer had a very low pre-inoculation number of LPS-specific ASC. We conclude that strain 638 elicits a significant immune response.

TABLE 3

Frequency of occurrence of adverse reactions after ingestion of El Tor Ogawa candidate vaccine strain 638.

| Symptom | Group of volunteers | | | | | | Probability |
|---|---|---|---|---|---|---|---|
| | Inoculated[1] | | Placebo[2] | | | Confidence | |
| | + | − | + | − | R.R.[3] | interval[4] | (Fisher) |
| Diarrhea | 4 | 38 | 1 | 13 | 1.33 | 0.16– | 0.6329 |
| Abdominal cramps | 13 | 29 | 2 | 12 | 2.17 | 0.56–8.44 | 0.1944 |
| Gurgling | 14 | 28 | 3 | 11 | 1.56 | 0.52–4.63 | 0.3143 |
| Heartburn | 6 | 36 | 2 | 12 | 1.00 | 0.23–4.40 | 0.6850 |
| Headache | 7 | 35 | 0 | 14 | — | — | 0.1163 |
| Vomiting | 1 | 41 | 0 | 14 | — | — | 0.7500 |

| | Volunteers with diarrhea |
|---|---|
| Mean diarrheal stool weight (range) | 425 g (220–680) |
| Mean number of diarrheal stools per ill volunteer (range) | 2 (1–5) |

Notes:
[1]N = 42,
[2]N = 14,
[3]Relative Risk,
[4](95%).

TABLE 4

Recovery of *Vibrio cholerae* strain 638 from the stools of volunteers.

| Group of Volunteers | Volunteers excreting vaccine strain/total | | | | | | Mean CFU/g stool |
|---|---|---|---|---|---|---|---|
| | Time after inoculation (h) | | | | | | |
| | 24 | 48 | 72 | 96 | 120 | Total | |
| High dose (1–2 × 10$^9$) | 7/29 | 11 | 16/29 | 15/29 | 10/29 | 28/2 | 4.4 × 10$^6$ |
| Medium dose (2 × 10$^8$) | 6/6 | 5/6 | 4/6 | 4/6 | 3/6 | 6/6 | 5.5 × 10$^6$ |
| Low dose (4 × 10$^7$) | 1/7 | 2/7 | 2/7 | 2/7 | 2/7 | 3/7 | 2.7 × 10$^5$ |

TABLE 5

Anti-LPS IgA ASC response in peripheral blood of volunteers following ingestion of *Vibrio cholerae* strain 638.

| Dose | Positives (%) | Mean ASC per 10$^7$ PBMC (range) |
|---|---|---|
| High | 27/29 (93.1) | 485 (0–4750) |
| Medium | 6/6 (100) | 377 (40–1285) |
| Low | 6/7 (85.7) | 5 (0–65) |
| Placebo | 1/14 (7.1) | 371 (0–2040) |

TABLE 6

Serum antibody responses in volunteers orally administered *Vibrio cholerae* El Tor Ogawa strain 638

| Response | Group of volunteers | | | |
|---|---|---|---|---|
| | High dose | Medium dose | Low dose | Placebo |
| Vibriocidal antibodies | | | | |
| Seroconversion rate[1] (%) | 24/29 (82) | 5/6 (83) | 5/7 (71) | 0/14 (0) |
| GMT (range): | | | | |
| Pre-inoculation | 47 (0–160) | 32 (0–40) | 33 (0–40) | 37 (0–320) |
| Post-inoculation peak [14 days] | 873 (0–20480) | 639 (0–2560) | 389 (40–2560) | 46 (0–320) |
| Responders with titers $\geq$ 1024 | 10/24 | 4/5 | 4/5 | 0 |
| Anti-Ogawa LPS IgG | | | | |
| Seroconversion rate[2] (%) | 23/29 (79) | 4/6 (67) | 3/7 (44) | 1/14 (7) |
| Log reciprocal titer[3] ± SD: | | | | |
| Pre-inoculation | 0.12 ± 0.25 | 0.12 ± 0.29 | 0 | 0.03 ± 0.12 |
| Post-inoculation Peak [14 days] | 1.86 ± 1.12 | 1.59 ± 1.49 | 1.07 ± 1.36 | 0.19 ± 0.57 |
| Anti-Ogawa LPS IgA | | | | |
| Seroconversion rate[2] (%) | 26/29 (90) | 6/6 (100) | 5/7 (71) | 0/14 (0) |
| Log reciprocal titer[3] ± SD: | | | | |
| Pre-inoculation | 0.1 ± 0.37 | 0 | 0.27 ± 0.37 | 0.13 ± 0.39 |
| Post-inoculation peak [14 days] | 2.43 ± 1.0 | 2.68 ± 0.48 | 1.96 ± 1.25 | 0.19 ± 0.53 |

Notes:
[1] Number of volunteers with fourfold increase in titer/total,
[2]Number of volunteers with a twofold increase in titer/total,
[3]logarithm of the reciprocal arithmetic mean titer.
Abbreviations:
GMT, geometric mean titer;
SD, standard deviation of the mean.

IV EXAMPLES

The examples described herein were conceived to illustrate rather than to limit the invention.

Constructing Safe Vaccine Candidates From Non-toxigenic Parentals

For constructing Hemagglutinin/Protease defective derivatives from non-toxigenic mutants described in table 1a, each parental strain was equally processed. First, suicide vector pGPH6 (FIG. 4) containing the HA/P gene (hap) inactivated by insertion of reporter gene celA was transferred from *E. coli* SM10λpir to the non-toxigenic mutant to produce an ampicillin resistant co-integrate. Second, Southern hybridization demonstrated the co-integrate to contain the insertionally inactivated hap gene (hap::celA) and its wild type allele (hap) separated by vector DNA. Third, the above ampicillin-resistant co-integrate was allowed to segregate in antibiotic-free medium and ampicillin-sensitive colonies selected. Ampicillin-sensitive colonies designated 638, 1333 and L911, were characterized by Southern analysis and shown to contain the hap::celA mutant allele.

Constructing 638T a Thymidilate Synthase Defective Derivative of *Vibrio cholerae* Strains 638.

For constructing mutants of *Vibrio cholerae* which are defective in the expression of Thymidilate Synthase, its coding gene thyA was first cloned and sequenced. ThyA gene from *Vibrio cholerae* was first cloned by complementing a spontaneous trimethoprim-resistant thymidine-requiring mutant of strain 81, with a genomic library of strain C7258 constructed in pBR322. One clone was selected, purified and the insert brought to pUC19 which served as template to facilitate sequencing with universal primers. Nucleotide sequence of thyA gene and its predicted polypeptide of Thymidilate Synthase (TSasa) protein are shown in SEQ ID NO 1.

To construct a TSasa defective vaccine strain, an internal restriction fragment was deleted "in vitro" from the thyA open reading frame. Deletion comprised nucleotides between MluI and BglII restriction sites and removed DNA sequences coding for amino acid 7 to amino acid 105 of ThyA protein. The resultant gene construct was impaired in its ability to complement the thyA defect of spontaneous mutant *Vibrio cholerae* 815.

Figure 5:
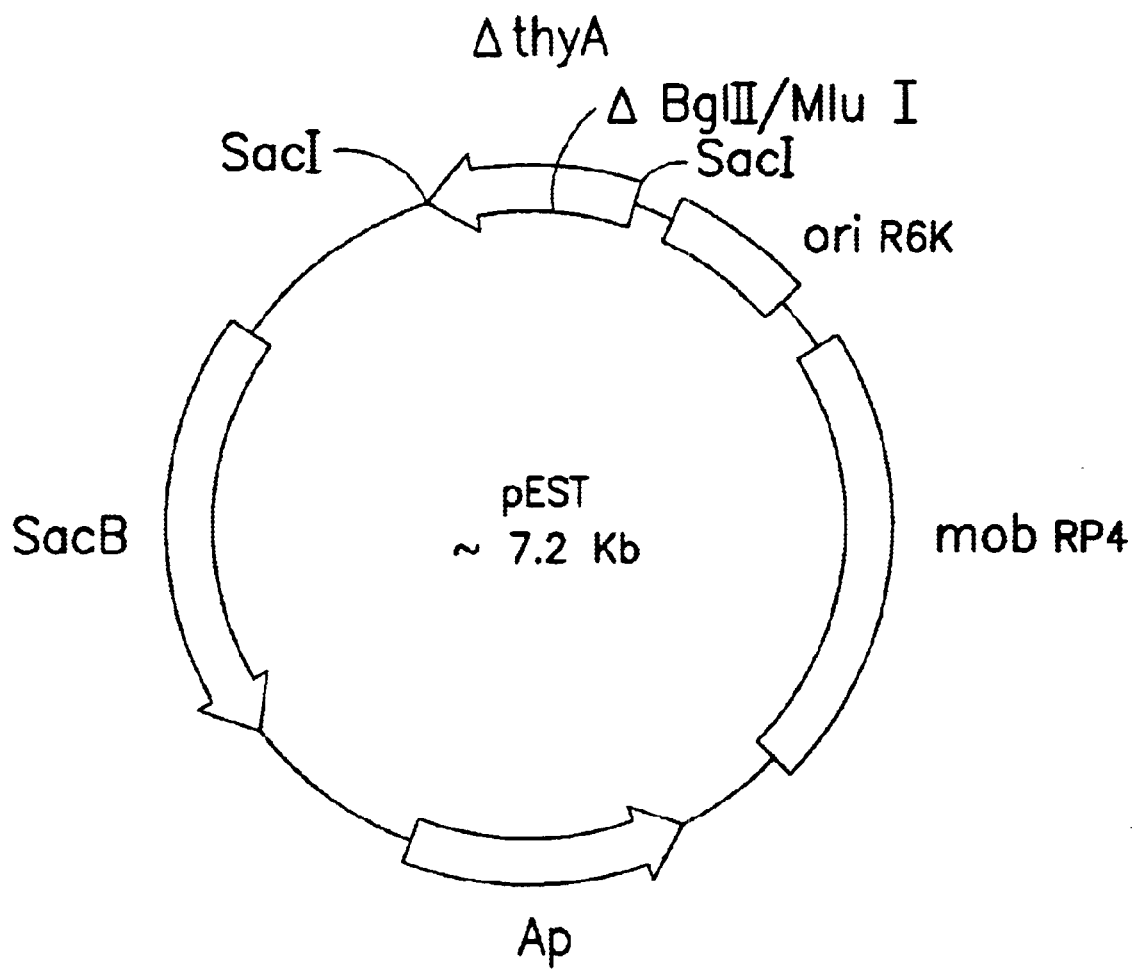

This fragment was cloned into the unique Sacd restriction site of pCVD442 to obtain pEST (FIG. 5). This plasmid was transferred from *E. coli* SM10λpir *Vibrio cholerae* strain 638 and an ampicillin-resistant co-integrate was selected. Southern analysis of the co-integrate demonstrated pEST was specifically integrated within the thyA gene. The ampicillin-resistant co-integrate was allowed to segregate in antibiotic-free medium supplemented with thymidine. Sucrose-resistant colonies were selected in the presence of thymidine. A thymidine-requiring, ampicillin-sensitive colony designated 638T, was characterized by Southern analysis and demonstrated to contain the dysfunctional thyA allele. pEST was used to construct 638T and will also be useful for constructing 1333T, and L911T or any additional defined thyA defective derivative other *V. cholerae* strain.

A brief description of the drawings follows.

FIG. 1. Detection of cholerae vibrios tagged with celA in plate assays employing CMC-indicator agar.

Figure 2:

FIG. 2. Detection of flagella on *Vibrio cholerae* mutant L911 of the O139 serogroup.

Figure 3:

FIG. 3. Detection of TCP on bacterial surface of 638T.

Figure 4:
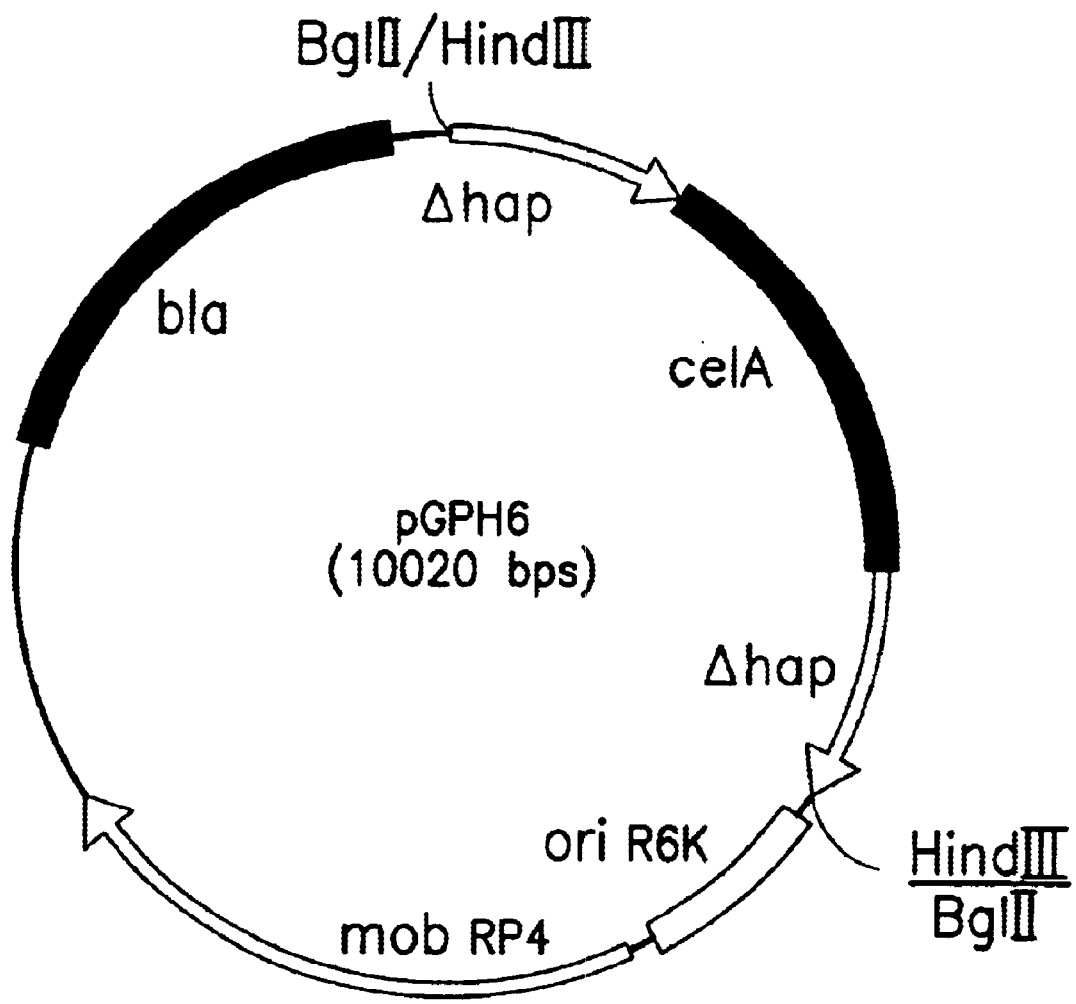

FIG. 4. Schematic representation of suicide vector pGPH6 used to construct hap::celA mutants of *V. cholerae*.

FIG. 5. Schematic representation of suicide vector of pEST used to construct thyA mutants.

ADVANTAGES

This invention provides us with an approach to create safer mutants of *Vibrio cholerae* by inactivation of the hemagglutinin/protease gene of non-toxigenic mutants. Such derivatives are useful as vaccines.

Safety and immunogenicity of strains 638, 1333 and L911 are similar to that presented in patent WO 95/18633. Additionally they are representative of all *Vibrio cholerae* strains circulating during the current pandemic and of the new O139 serogroup. Said strains are also tagged with a distinguishable marker to facilitate environmental sampling of the vaccine. All mutations introduced to construct the: vaccines described herein are well defined as gene deletions or as gene insertions of known nature.

This invention also provides a method to improve the environmental biosafety of live cholera strains to be used as oral vaccines. This improvement is attained by creating a defined mutation in the gene thyA which is also described herein.

Vaccine strain 638T is featured by its enhanced environmental biosafety. It has a thymidine auxotrophy that limits its proliferation in natural ecosystems, where free pyrimidines are scarce if existent.

Trimethoprim resistance conferred to *Vibrio cholerae* vaccine candidate 638T by its mutant thyA gene is unlikely to be transmitted into other bacteria due to its recessive nature. Additionally, resistance to trimethoprim is conditioned to the presence of thymine or thymidine in a culture.

Reacquisition of cholerae toxin genes or other DNA by means of horizontal gene transfer is superfluous in these strains since they do not proliferate out from the laboratory.

V. Deposits

Under the terms of the Budapest Treaty on the International Recognition of the Deposit of Microorganisms for the Purpose of the Patent Procedure, deposits of *Vibrio cholerae* strains described herein have been made with the DSMZ-Deutsche Sammlung von Mikrooganismen und Zelikulturen Gmbh (German Collection of Microorganisms and Cell Cultures), Braunschweig; Federal Republic of Germany as follows:

| | |
|---|---|
| *Vibrio cholerae* 1333 | DSM 12757 |
| *Vibrio cholerae* L911 | DSM 12758 |
| *Vibrio cholerae* 638 | DSM 12759 |
| *Vibrio cholerae* 638T | DSM 12760 |

All the deposits were made on Apr. 7, 1999.

What is claimed is:

1. A method of producing a mutant strain of *Vibrio cholerae* from a non-toxigenic mutant of *Vibrio cholerae*, the mutant strain being suitable for administration to humans, the method comprising the steps of:
   1) inactivating hap gene of said non-toxigenic mutant of *Vibrio cholerae* by a defined irreversible genetic manipulation; and
   2) introducing into thyA gene of said non-toxigenic mutant of *Vibrio cholerae* a defined irreversible genetic manipulation, wherein the defined irreversible genetic manipulation comprises deleting nucleotides from said thyA gene between MluI and BglII restriction sites (SEQ ID NO: 1).

2. The method of claim 1, wherein the step of inactivating the *Vibrio cholerae* hap gene comprises disrupting the *Vibrio cholerae* hap gene with celA gene.

3. A method of producing a mutant strain of *Vibrio cholerae* from a non-toxigenic mutant of *Vibrio cholerae*, the mutant strain being suitable for administration to humans, the method comprising the steps of:
   1) inactivating hap gene of said non-toxigenic mutant of *Vibrio cholerae* by a defined irreversible genetic manipulation, wherein the step of inactivating comprises disrupting said hap gene with celA gene; and
   2) introducing into thyA gene of said non-toxigenic mutant of *Vibrio cholerae* a defined irreversible genetic manipulation, wherein said manipulation comprises deleting nucleotides from said thyA gene between MluI and BglII restriction sites (SEQ ID NO: 1).

* * * * *

SEQUENCE LISTING

<160> NUMBER OF SEQ ID NOS: 2

<210> SEQ ID NO 1
<211> LENGTH: 852
<212> TYPE: DNA
<213> ORGANISM: Vibrio cholerae

<400> SEQUENCE: 1

| | | | | | |
|---|---|---|---|---|---|
| gtgagacagt | atttagatct | ttgtcagcgc | atcgtcgatc | aaggtgtttg | ggttgaaaat | 60 |
| gaacgaacgg | gcaagcgttg | tttgactgtg | attaatgccg | atttgaccta | cgatgtgggc | 120 |
| aacaatcagt | ttcctctagt | cactacacgc | aagagttttt | ggaaagccgc | cgtggccgag | 180 |
| ttgctcggct | atattcgtgg | ttacgataat | gcggcggatt | ttcgccaatt | aggtaccaaa | 240 |
| acctgggatg | ctaatgccaa | tttaaaccaa | gcatggctca | acaatcctta | ccgtaaaggt | 300 |
| gaggatgaca | tgggacgcgt | gtatggagtt | cagggtagag | cttgggctaa | gcctgatggt | 360 |
| ggtcatattg | accagttgaa | aaagattgtt | gatgatttga | gccgtggcgt | tgatgaccga | 420 |
| ggtgaaattc | ttaacttcta | caatccgggt | gaatttcaca | tggggtgttt | gcgcccttgc | 480 |
| atgtacagcc | atcattttc | attgctgggt | gataccttgt | atctcaacag | tactcagcgt | 540 |
| tcatgtgatg | tgcccttggg | gttgaatttc | aacatggtgc | aggtttatgt | gttccttgcg | 600 |
| ctgatggcac | agatcacagg | gaaaaagccg | ggcttggcgt | atcacaagat | cgtcaatgcg | 660 |
| cacatttacc | aagatcaact | cgaattgatg | cgcgatgtgc | agctaaaacg | tgagccattc | 720 |
| ccagcgcctc | agttccatat | caatccaaag | attaaaacac | tgcaggattt | ggaaacttgg | 780 |
| gtcactttgg | atgattttga | cgtcaccgga | tatcagttcc | acgatcctat | tcaataccccg | 840 |
| ttttcagtct | aa | | | | | 852 |

<210> SEQ ID NO 2
<211> LENGTH: 283
<212> TYPE: PRT
<213> ORGANISM: Vibrio cholerae

<400> SEQUENCE: 2

Val Arg Gln Tyr Leu Asp Leu Cys Gln Arg Ile Val Asp Gln Gly Val
1               5                   10                  15

Trp Val Glu Asn Glu Arg Thr Gly Lys Arg Cys Leu Thr Val Ile Asn
            20                  25                  30

Ala Asp Leu Thr Tyr Asp Val Gly Asn Asn Gln Phe Pro Leu Val Thr
        35                  40                  45

Thr Arg Lys Ser Phe Trp Lys Ala Ala Val Ala Glu Leu Leu Gly Tyr
    50                  55                  60

Ile Arg Gly Tyr Asp Asn Ala Ala Asp Phe Arg Gln Leu Gly Thr Lys
65                  70                  75                  80

Thr Trp Asp Ala Asn Ala Asn Leu Asn Gln Ala Trp Leu Asn Asn Pro
                85                  90                  95

Tyr Arg Lys Gly Glu Asp Asp Met Gly Arg Val Tyr Gly Val Gln Gly
            100                 105                 110

Arg Ala Trp Ala Lys Pro Asp Gly Gly His Ile Asp Gln Leu Lys Lys
        115                 120                 125

Ile Val Asp Asp Leu Ser Arg Gly Val Asp Asp Arg Gly Glu Ile Leu
    130                 135                 140

Asn Phe Tyr Asn Pro Gly Glu Phe His Met Gly Cys Leu Arg Pro Cys
145                 150                 155                 160

-continued

```
Met Tyr Ser His His Phe Ser Leu Leu Gly Asp Thr Leu Tyr Leu Asn
            165                 170                 175

Ser Thr Gln Arg Ser Cys Asp Val Pro Leu Gly Leu Asn Phe Asn Met
            180                 185                 190

Val Gln Val Tyr Val Phe Leu Ala Leu Met Ala Gln Ile Thr Gly Lys
        195                 200                 205

Lys Pro Gly Leu Ala Tyr His Lys Ile Val Asn Ala His Ile Tyr Gln
    210                 215                 220

Asp Gln Leu Glu Leu Met Arg Asp Val Gln Leu Lys Arg Glu Pro Phe
225                 230                 235                 240

Pro Ala Pro Gln Phe His Ile Asn Pro Lys Ile Lys Thr Leu Gln Asp
            245                 250                 255

Leu Glu Thr Trp Val Thr Leu Asp Asp Phe Asp Val Thr Gly Tyr Gln
            260                 265                 270

Phe His Asp Pro Ile Gln Tyr Pro Phe Ser Val
            275                 280
```